United States Patent

Kaneko et al.

[11] Patent Number: 5,821,362
[45] Date of Patent: Oct. 13, 1998

[54] METHOD OF DESILYLATING SILYLETHER COMPOUNDS

[75] Inventors: Akira Kaneko; Tsutomu Kaku, both of Niigata-ken; Masaji Ishiguro, Hyogo-ken; Takashi Nakatsuka, Osaka, all of Japan

[73] Assignee: Suntory Limited, Osaka, Japan

[21] Appl. No.: 579,453

[22] Filed: Dec. 27, 1995

Related U.S. Application Data

[63] Continuation of Ser. No. 194,420, Feb. 10, 1994, abandoned.

[30] Foreign Application Priority Data

Feb. 12, 1993 [JP] Japan .................................. 5-024245

[51] Int. Cl.$^6$ ...................... C07D 487/00; C07D 487/04; C07D 499/00
[52] U.S. Cl. ........................... 540/302; 540/304; 540/310; 540/350; 548/152; 548/178
[58] Field of Search ................... 548/178, 152; 540/302, 304, 310, 350

[56] References Cited

U.S. PATENT DOCUMENTS

| | | | |
|---|---|---|---|
| 4,992,460 | 2/1991 | Fleet ........................................ | 514/413 |
| 5,023,340 | 6/1991 | Fleet ........................................ | 548/453 |
| 5,260,438 | 11/1993 | Horikawa et al. ...................... | 540/302 |
| 5,414,081 | 5/1995 | Horikawa et al. ...................... | 540/302 |
| 5,587,474 | 12/1996 | Kondo et al. ........................... | 540/350 |

FOREIGN PATENT DOCUMENTS

| | | |
|---|---|---|
| 0567949 | 3/1993 | European Pat. Off. . |
| 8-27152 | 1/1996 | Japan . |

OTHER PUBLICATIONS

Nicolaou et al., J. Org. Chem., vol. 44, No. 22, 1979, pp. 4011–4013.
Trost et al., Tet. Lett., vol. 22, No. 50, 1981, pp. 4999–5002.
Masamune et al., J. Am. Chem. Soc., vol. 104, No. 20, 1982, pp. 5523–5526.
Anker, Carbo. Res., vol. 166, No. 2, 1987, pp. 309–313.
Aldrich Catalog Handbook of Fine Chemicals, Compound 18,422–5, p. 828, 1988.
Giudicelli et al., Tet. Lett., vol. 31, No. 45, 1990, pp. 6527–6530.
Greene et al., Protective Groups in Organic Synthesis, 2$^{nd}$ ed., 1991, pp. 77–84.
Tetrahedron Letters, vol. 26, No. 5, 1985, Oxford GB pp. 681–684, E.W. Collington, et al. "Selective deprotection of alcoholic and phenolic silyl ethers".
Journal of the American Chemical Society, vol. 94, No. 17, 23 Aug. 1972, Gaston, PA US pp. 6190–6191, E.J. Corey et al, "Protection of hydroxyl groups as tert–butyldimethylsilyl derivatives".

*Primary Examiner*—Shean C. Wu
*Attorney, Agent, or Firm*—Pillsbury, Madison & Sutro, IP Group of Cushman, Darby & Cushman

[57] ABSTRACT

Method of desilylating a silylether compound by reacting a silylether compound of the general formula (I):

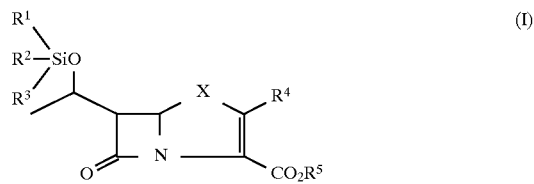

or a salt thereof with an amine hydrogen fluoride salt or a pyridine hydrogen fluoride salt in an organic solvent to produce a compound of the general formula (IV):

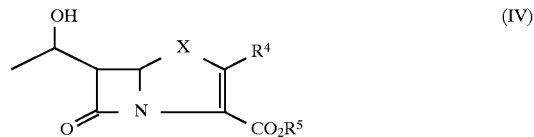

According to this method, silylether compounds that are labile under strong acidic or basic conditions can be desilylated efficiently using inexpensive reagents.

6 Claims, No Drawings

METHOD OF DESILYLATING SILYLETHER COMPOUNDS

This is a continuation of application Ser. No. 8/194,420, filed on Feb. 10, 1994, now abandoned.

BACKGROUND OF THE INVENTION

This invention relates to a method of desilylating silylether compounds.

Various conventional methods are known to be applicable for desilylating silylether compounds and they include:

(1) a method in which a quaternary ammonium fluoride such as tetra-n-butylammonium fluoride (n-Bu$_4$NF) is caused to act in an organic solvent such as tetrahydrofuran (J. Am. Chem. Soc., 1972, 94, 6190);

(2) a method in which a mineral acid or a strong organic acid is caused to act in an anhydrous organic solvent such as acetonitrile or a hydrous organic solvent (Japanese Patent Public Disclosure (KOKAI) No. Hei 1-83633);

(3) a method in which N-bromosuccinimide (NBS) is caused to act in dimethyl sulfoxide (DMSO) (Synthesis, 1980, 234);

(4) a method in which a hydrogensulfate of an alkali metal is caused to act in a solvent such as water or alcohol (Japanese Patent Public Disclosure (KOKAI) No. Sho 62-120325);

(5) a method in which an aqueous solution of acetic acid is caused to act (J. Am. Chem. Soc., 1972, 94, 6190); and (6) a method in which excess potassium fluoride dihydrate is reacted with excess tetrabutylammonium chloride in acetonitrile (J. Chem. Soc. Chem. Comm. 1979, 514–5).

However, these conventional methods have their own problems. Methods (1) and (6) suffer from an economic disadvantage in that special and relatively expensive reagents such as n-Bu$_4$NF and tetrabutylammonium chloride must be used in more than an equivalent amount with respect to the silylether compound. Method (2) has the problem of low yield in the production of the end compound if the silylether compound to be treated has an acid-labile group. Method (3) is not applicable to silylether compounds that have an oxidation sensitive group. Method (4) is not highly suitable for treatment of compounds that are labile in protonic solvents or the intended reaction will not progress efficiently with such compounds.

SUMMARY OF THE INVENTION

Under the circumstances, the present inventors conducted intensive studies in order to develop an alternative method of desilylating silylether compounds that uses inexpensive and safe reagents and which are applicable not only to acid-stable compounds but also to those compounds which are fairly labile in acids. As a result, the inventors found that silylether compounds could easily be desilylated by reacting them with hydrogen fluoride salts of amines in organic solvents. The present invention has been accomplished on the basis of this finding.

Thus, the present invention relates to a method of desilylating a silylether compound, which comprises reacting a silylether compound of the general formula (I):

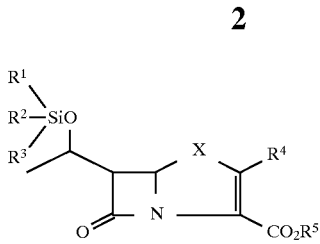

or a salt thereof where X is a methine substituted by an alkyl group having 1–3 carbon atoms, methylene or a sulfur atom; $R^1$, $R^2$ and $R^3$ which may be the same or different represent an alkyl group having 1–6 carbon atoms, an alkoxy group having 1–6 carbon atoms, an aryl group or an aralkyl group; $R^4$ represents a hydrogen atom, an optionally substituted lower alkyl group, an optionally substituted lower alkylthio group, an optionally substituted lower alkoxy group, an optionally substituted heterocyclic group, an optionally substituted heterocyclic lower alkyl group, an optionally substituted heterocyclic thio group, an optionally substituted heterocyclic lower alkylthio group, an optionally substituted aryl group, an optionally substituted aryloxy group or an optionally substituted aralkyl group; and $R^5$ represents a hydrogen atom or a carboxylic acid protecting group with an amine hydrogen fluoride salt of the general formula (II):

where $R^6$, $R^7$ and $R^8$ which may be the same or different represent an alkyl group having 1–8 carbon atoms, an aryl group, an aralkyl group or a hydrogen atom; n is the number of hydrogen fluorides inherent in an amine salt of interest or a pyridine hydrogen fluoride salt of the general formula (III);

where Py is an optionally substituted pyridine; n is the number of hydrogen fluorides inherent in a pyridine salt of interest in an organic solvent, thereby producing a compound of the general formula (IV):

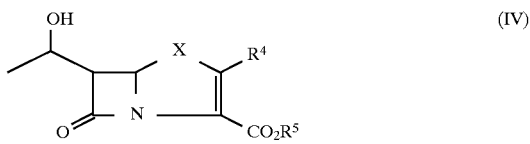

where X, $R^4$ and $R^5$ have the same meanings as defined above.

In the silylether compound of the general formula (I), X represents a methine substituted by an alkyl group having 1–3 carbon atoms, preferably by a methyl group, methylene or a sulfur atom;

$R^1$, $R^2$ and $R^3$ which may be the same or different represent an alkyl group having 1–6, preferably 1–4 carbon atoms, for example, a methyl group, an ethyl group, a n-propyl group, an isopropyl group, a n-butyl group, a tert-butyl group and a hexyl group; an alkoxy group having 1–6, preferably 1–4 carbon atoms, for example, a methoxy group and an ethoxy group; an aryl group, preferably an aryl group having 6–10 carbon atoms such as a phenyl group and a cumenyl group; or an aralkyl group, preferably an aralkyl group having 6–10 carbon atoms such as a benzyl group and a phenethyl group; and $R^4$ represents a hydrogen atom, an optionally substituted lower alkyl group, an optionally substituted lower alkylthio group, an optionally substituted lower alkoxy group, an optionally substituted heterocyclic group, an optionally substituted heterocyclic lower alkyl group, an optionally substituted heterocyclic thio group, an optionally substituted heterocyclic lower alkylthio group, an optionally substituted aryl group, an optionally substituted aryloxy group or an optionally substituted aralkyl group.

In the above-mentioned definition of $R^4$, "lower" means, preferably, 1–6 carbon atoms, more preferably, 1–4 carbon atoms. Examples of a preferred lower alkyl group include a methyl group, an ethyl group, an n-propyl group, an isopropyl group, an n-butyl group and a tert-butyl group. Examples of a preferred aryl group include an aryl group having 6–10 carbon atoms such as a phenyl group and a cumenyl group. Examples of a preferred aralkyl group include an aralkyl group having 6–10 carbon atoms such as a benzyl group and a phenethyl group. These alkyl, aryl and aralkyl groups may have one or more substituents selected from a halogen atom such as a fluorine atom, a chlorine atom and a bromine atom, a lower alkyl group such as methyl group and an ethyl group, a lower alkoxy group such as a methoxy group and an ethoxy group, an acyloxy group having 2–11 carbon atoms such as an acetoxy group and a benzoyloxy group, an amino group, an amino lower alkyl group, a carbamoyl group, a carbamoyloxy group, an imino lower alkylamino group, a heterocyclic group to be mentioned below, a heterocyclic lower alkyl group and the like.

"Heterocyclic group" means a saturated or unsaturated monocyclic or polycyclic heterocyclic group having at least one hetero atom such as an oxygen atom, a sulfur atom and a nitrogen atom. Examples of a favorable heterocyclic group include: a 3–8 membered, particularly preferably, 5 or 6 membered unsaturared monocyclic heterocyclic group having 1–4 nitrogen atoms such as a pyrrolyl group, a pyrrolinyl group, an imidazolyl group, a pyrazolyl group, a pyridyl group and the N-oxide thereof, a pyrimidyl group, a pyrazinyl group, a pyridazinyl group, a triazolyl group such as a 4H-1,2,4-triazolyl group, a 1H-1,2,3-triazolyl group and a 2H-1,2,3-triazolyl group, a tetrazolyl group such as a 1H-tetrazolyl group and a 2H-tetrazolyl group, and a dihydrotriazinyl group such as 4,5-dihydro-1,2,4-triazinyl group and 2,5-dihydro-1,2,4-triazinyl group; a 3–8 membered, particularly preferably, 5 or 6 membered saturated monocyclic heterocyclic group having 1–4 nitrogen atoms such as an azetidinyl group, a pyrrolidinyl group, an imidazolidinyl group, a piperidinyl group, a pyrazolidinyl group and a piperadinyl group; a 7–12 membered unsaturared polycyclic heterocyclic group having 1–5 nitrogen atoms such as an indolyl group, an isoindolyl group, an indolidinyl group, a benzimidazolyl group, a quinolyl group, an isoquinolyl group, an indazolyl group, a benzotriazolyl group, a tetrazolopyridyl group, a tetrazolopyridazinyl group such as a tetrazolo[1,5-b]pyridazinyl group, and a dihydrotriazolopyridazinyl group; a 3–8 membered, particularly preferably, 5 or 6 membered unsaturared monocyclic heterocyclic group having 1 or 2 oxygen atoms and 1–3 nitrogen atoms such as an oxazolyl group, an isoxazolyl group and an oxadiazolyl group such as a 1,2,4-oxadiazolyl group, 1,3,4-oxadiazolyl group and 1,2,5-oxadiazolyl group; a 3–8 membered, particularly preferably, 5 or 6 membered saturated monocyclic heterocyclic group having 1 or 2 oxygen atoms and 1–3 nitrogen atoms such as a morpholinyl group; a 7–12 membered unsaturared polycyclic heterocyclic group having 1 or 2 oxygen atoms and 1–3 nitrogen atoms such as a benzoxazolyl group and a benzoxadiazolyl group; a 3–8 membered, particularly preferably, 5 or 6 membered unsaturared monocyclic heterocyclic group having 1 or 2 sulfur atoms and 1–3 nitrogen atoms such as a 1,3-thiazolyl group, a 1,2-thiazolyl group, a thiazolinyl group, and a thiadiazolyl group such as 1,2,4-thiadiazolyl group, 1,3,4-thiadiazolyl group, 1,2,5-thiadiazolyl group and 1,2,3-thiadiazolyl group; a 3–8 membered saturated monocyclic heterocyclic group having 1 or 2 sulfur atoms and 1–3 nitrogen atoms such as a thiazolidinyl group; a 7–12 membered unsaturared polycyclic heterocyclic group having 1 or 2 sulfur atoms and 1–3 nitrogen atoms such as a benzothiazolyl group and a benzothiadiazolyl group; a 3–8 membered, particularly preferably, 5 or 6 membered unsaturared monocyclic heterocyclic group having 1 or 2 oxygen atoms such as a furanyl group and a pyranyl group; a 3–8 membered, particularly preferably, 5 or 6 membered saturated monocyclic heterocyclic group having 1 or 2 oxygen atoms such as a tetrahydrofuranyl group and a tetrahydropyranyl group; a 3–8 membered, particularly preferably, 5 or 6 membered unsaturared monocyclic heterocyclic group having 1 or 2 sulfur atoms such as a thienyl group and the S-oxide thereof; and a 3–8 membered, particularly preferably, 5 or 6 membered saturated monocyclic heterocyclic group having 1 or 2 sulfur atoms such as a tetrahydrothienyl group and the S-oxide thereof. These heterocyclic groups may have one or more substituents selected from a halogen atom such as a fluorine atom, a chlorine atom and a bromine atom, a lower alkyl group such as a methyl group and an ethyl group, a lower alkoxy group such as a methoxy group and an ethoxy group, a lower alkenyl group such as an allyl group and a propenyl group, an acyloxy group having 2–11 carbon atoms such as an acetoxy group and a benzoyloxy group, an amino group, an amino lower alkyl group, a carbamoyl group, a carbamoyloxy group and an imino lower alkyl group. Concrete examples of R4 are shown below.

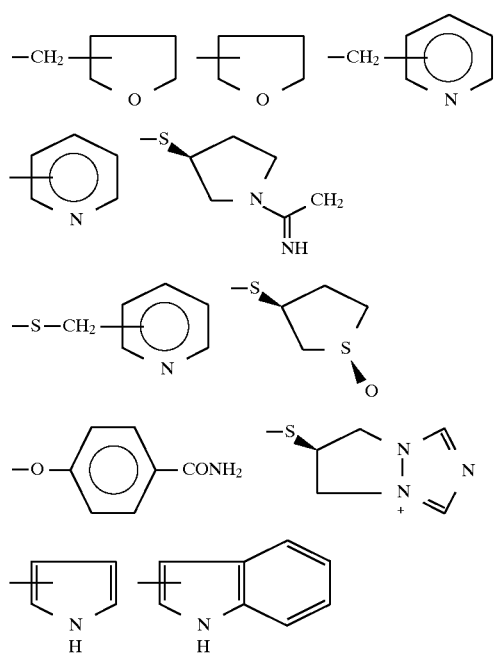

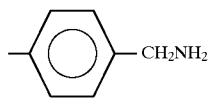

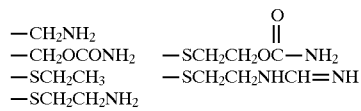

In the silylether compound of the general formula (I), $R^5$ represents a hydrogen atom or a carboxylic acid protecting group.

This protecting group is not particularly limited, as long as it is used in the technical field of β-lactam compounds. For the purpose of protecting a carboxylic acid, any group may be used that can form an ester together with the carboxylic acid and that can be eliminated by hydrolysis, photolysis, oxidation or reduction or enzymatically be eliminated.

Examples of preferred groups are those which form the following esters: a lower alkyl ester such as a methyl ester, an ethyl ester, an n-propyl ester, an isopropyl ester, an n-butyl ester, an isobutyl ester, a tert-butyl ester, a pentyl ester and a hexyl ester, a lower alkyl ester optionally having at least one suitable substituent such as a lower alkanoyloxy-lower alkyl ester, for example, an acetoxymethyl ester, a propionyloxymethyl ester, a butyryloxymethyl ester, a valeryloxymethyl ester, a pivaloyloxymethyl ester, a hexanoyloxymethyl ester, a 1-or 2-acetoxyethyl ester, a 1- or 2- or 3-acetoxypropyl ester, a 1- or 2- or 3- or 4-acetoxybutyl ester, a 1- or 2-propionyloxyethyl ester, a 1- or 2- or 3-propionyloxypropyl ester, a 1- or 2-butyryloxyethyl ester, a 1- or 2-isobutyryloxyethyl ester, a 1- or 2-pivaloyloxyethyl ester, a 1- or 2-hexanoyloxyethyl ester, an isobutyryloxymethyl ester, a 2-ethylbutyryloxymethyl ester, a 3,3-dimethylbutyryloxymethyl ester and a 1- or 2-pentanoyloxyethyl ester, a lower alkanesulfonyl- lower alkyl ester, for example, a 2-mesylethyl ester, a mono or di or trihalo-lower alkyl ester, for example, a 2-iodoethyl ester, a 2,2-dichloroethyl ester and a 2,2,2-trichloroethyl ester, a lower alkoxycarbonyloxy-lower alkyl ester, for example, a methoxycarbonyloxymethyl ester, an ethoxycarbonyloxymethyl ester, a propoxycarbonyloxymethyl ester, a tert-butoxycarbonyloxymethyl ester, a 1- or 2-methoxycarbonyloxyethyl ester, a 1- or 2-ethoxycarbonyloxyethyl ester and a 1- or 2-isopropoxycarbonyloxyethyl ester, a phthalidytidene-lower alkyl ester, or a 5-loweralkyl-2-oxo-1,3-dioxolen-4-yl lower alkyl ester, for example, a 5-methyl-2-oxo-1,3-dioxolen-4-yl methyl ester, a 5-ethyl-2-oxo-1,3-dioxolen-4-yl methyl ester, a 5-propyl-2-oxo-1,3-dioxolen-4-yl ethyl ester; a lower alkenyl ester, for example, a vinyl ester and an allyl ester; a lower alkynyl ester, for example, an ethynyl ester and a propynyl ester; an aryl lower alkyl ester optionally having at least one suitable substituent, for example, a benzyl ester, a 4-methoxybenzyl ester, a 4-nitrobenzyl ester, a phenethyl ester, a trityl ester, a benzhydryl ester, a bis (methoxyphenyl)methyl ester, a 3,4-dimethoxybenzyl ester and a 4-hydroxy-3,5-di-tert -butylbenzyl ester; an aryl ester optionally having at least one suitable substituent, for example, a phenyl ester, a 4-chlorophenyl ester, a tolyl ester, a tert-butylphenyl ester, a xylyl ester, a mesityl ester and a cumenyl ester; and a phthalidyl ester.

The salt of a silylether compound represented by the general formula (I) may be a common salt. Examples of such a salt include a salt with a base such as an alkali metal salt, for example, a sodium salt and a potassium salt, an alkaline earth metal salt, for example, a calcium salt and a magnesium salt, a salt with an inorganic base such as an ammonium salt, a salt with an organic base such as an organic amine salt, for example, a triethylamine salt, a pyridine salt, a picoline salt, an ethanolamine salt, a triethanolamine salt, a dicyclohexylamine salt and an N,N'-dibenzylethylenediamine salt; a salt with an acid such as an inorganic acid addition salt, for example, a hydrochloride, a hydrobromide, a sulfate and a phosphate and an organic acid addition salt, for example, a formate, an acetate, a trifluoroacetate, a maleate, a tartrate, a methanesulfonate and a benzenesulfonate; a salt with a basic or acidic amino acid such as arginine, aspartic acid and glutamic acid; and an intermolecular or intramolecular quaternary salt.

In an amine hydrogen fluoride salt of the general formula (II), $R^6$, $R^7$ and $R^8$ which may be the same or different represent an alkyl group having 1–8, preferably, 1–4 carbon atoms such as a niethlyl group, an ethyl group, a propyl group, an isopropyl group, a butyl group and a tert-butyl group; an aryl group, preferably, an aryl group having 6–10 carbon atoms such as a phenyl group and a cumenyl group; an aralkyl group, preferably, an aralkyl group having 6–10 carbon atoms such as a benzyl group and a phenethyl group; or a hydrogen atom, and n is the number of hydrogen fluorides inherent in an amine salt of interest.

In a pyridine hydrogen fluoride salt of the general formula (III), Py represents an optionally substituted pyridine, which may have one or more substituents defined above regarding the heterocyclic group, and n is the number of hydrogen fluorides inherent in a pyridine salt of interest.

The method of the present invention can be implemented under neutral to weakly acidic conditions and, hence, it is favored by starting compounds or final products that are labile under basic or strong acidic conditions. Hence, alcoholic compounds can generally be produced in high yield by the method of the present invention.

DETAILED DESCRIPTION OF THE INVENTION

The silyl groups that can advantageously be removed by the method of the present invention have the structure recited in claim 1 and typical silyl groups are a trialkylsilyl group, an arylalkylalkoxysilyl group, an alkoxydiarylsilyl group, a triarylsilyl group, an alkyldiarylsilyl group, an aryldialkylsilyl group, a triaralkylsilyl group. Concrete examples of such silyl groups include a trimethylsilyl group, a triethylsilyl group, a triisopropylsilyl group, a dimethylhexylsilyl group, a tert-butyldimethylsilyl group, a methyldiisopropylsilyl group, an isopropyldimethylsilyl group, a tert-butylmethoxyphenylsilyl group, a tert-butoxydiphenylsilyl group, a triphenylsilyl group, a tert-butyldiphenylsilyl group, a dimethylcumenylsilyl group and a tribenzylsilyl group. Almost all silyl groups that are practical as alcohol protecting groups may effectively be removed by the method of the present invention.

The compounds that can be treated by the present invention have the structure recited in claim 1 and they embrace compounds that have not only the silylether group but also a carbonyl group, an ester group, an amide group, etc. and which are sensitive to acidic or basic conditions. Particularly preferred compounds are penem compounds of the general formula (V):

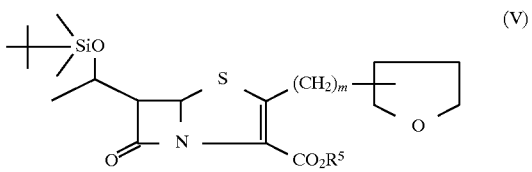

(V)

where R[5] has the same meaning as defined above; m is 0 or 1.

The compounds of the formula (V) can readily be synthesized by the methods described in prior art references such as Japanese Patent Public Disclosure (Kokai) No. Sho 61-207387, Japanese Patent Public Disclosure (Kokai) No. Sho 63-162694, WO92/03442, WO92/03443 and WO92/03444.

Any aprotic solvents that dissolve the compounds of the general formula (I) and which are inert to the starting materials and the end products may be used as organic solvents in the present invention. Advantageous solvents include: aromatic hydrocarbons such as benzene, toluene and xylene; chlorine-containing organic solvents such as methylene chloride, chloroform, ethane dichloride and monochlorobenzene; ketones such as acetone, methyl ethyl ketone and methyl isobutyl ketone; esters such as methyl acetate and ethyl acetate; nitriles such as acetonitrile and benzonitrile; and amides such as N,N-dimethylformamide. These solvents may be mixed either with themselves or with a small amount of water.

The reaction may be carried out at temperatures ranging from room temperature up to the boiling point of the reaction solvent used.

Various amine or pyridine hydrogen fluoride salts may be used in the present invention to permit the intended reaction to proceed smoothly. In this respect, particularly good results are attained with triethylamine trihydrogenfluoride or pyridine polyhydrogenflouride. To complete the reaction, these hydrogen fluoride salts need be used in at least one equivalent amount with respect to the silylether compound; preferably, 1.1–3.0 equivalents are used to insure smooth progress of the reaction.

The post-treatment of the reaction product may be performed in various ways. If the solvent used is sparingly or slightly soluble in water, the reaction mixture is directly washed with water so that a small excess of the hydrogen fluoride salt is rejected into water or, if necessary, the reaction mixture is first neutralized by washing with an aqueous solution of sodium hydrogencarbonate and, thereafter, re-washing with water is done and the solvent is distilled off, followed by the practice of a common isolation procedure such as column chromatography or recrystallization so as to produce the desired alcoholic compound in high yield. If the solvent used is water soluble, a small excess of the hydrogen fluoride salt is optionally neutralized with a base such as sodium hydrogencarbonate or ammonia and the resulting crystal is separated by filtration and replaced by a solvent sparingly or slightly soluble in water; thereafter, washing is done with water and the solvent is distilled off, followed by the practice of a common isolation procedure such as column chromatography or recrystallization so as to produce the end alcoholic compound in high yield. Since alcoholic compounds are synthesized in high yields by the method of the present invention, they need not be subjected to column chromatography, recrystallization or other purification procedures before they are used in the subsequent reaction.

The method of the present invention has as additional advantage in that an optically active silyether compound can be desilylated without losing its optical activity. Take, for example, (1'R,2"R,5R,6S)-6-(1'-tert-butyldimethytsilyloxy)-2-(2"-tetrahydrofuranyl)penem-3-carboxylic acid allyl ester, which is an optical active compound of the general formula (V). According to the present invention, the silyl group can be removed from this compound to yield (1'R,2"R,5R,6S)-6-(1'-hydroxyethyl)-2-(2"-tetrahydrofuranyl) penem-3-carboxylic acid allyl ester of high optical purity. Thus, the present invention provides an important method that is not only capable of desilylating various silyether compounds production of alcures the production of alcoholic compounds of high optical purity.

The following examples are provided for the purpose of further illustrating the present invention but are in no way to be taken as limiting.

EXAMPLE 1

Synthesis of (1'R,2"R,5R,6S)-6-(1'-hydroxyethyl)-2-(2"-tetrahydrofuranyl)penem-3-carboxylic acid allyl ester

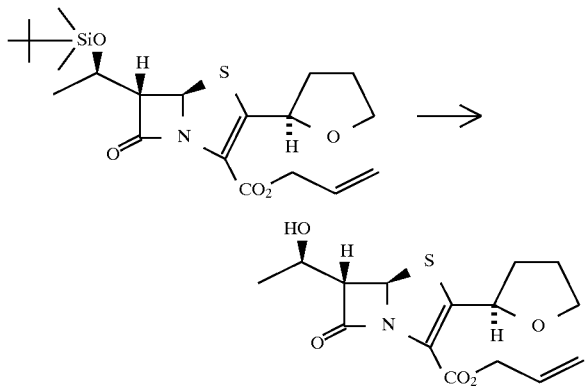

(1'R,2"R,5R,6S)-6-(1'-tert-butyldimethylsilyloxyethyl)-2-(2"-tetrahydrofuranyl)penem-3-carboxylic acid allyl ester (6.59 g, 15 mmol) was dissolved in methyl isobutyl ketone (15 ml) and triethylamine trihydrogenfluoride (3.63 g, 22.5 mmol) was added to the resulting solution. Thereafter, the solution was heated to 40° C. under stirring, which was continued for 6 h at the same temperature to complete the reaction. The reaction mixture was washed three times with water, once with 3% aqueous solution of sodium hydrogencarbonate and once with water, followed by drying on anhydrous magnesium sulfate. The solvent was distilled off and the resulting crude product was purified by silica gel column chromatography to yield the titled compound in an amount of 4.60 g (yield: 94.3%)

$^1$H—NMR (270 MHz, CDCl$_3$)

| | | | | |
|---|---|---|---|---|
| δ1.35 | d | 3H | J = 6Hz | 2' position-CH$_3$ |
| 1.62 | s | 1H | | -OH |
| 1.75–2.05 | m | 4H | | |
| 2.42–2.52 | m | 1H | | |
| 3.71 | d, d | 1H | J = 6Hz | 6 position-H |
| 3.81–3.89 | m | 1H | | |
| 3.93–4.02 | m | 1H | | |
| 4.16–4.26 | m | 1H | | 1' position-H |
| 4.65 and 4.77 | t, d, d | each 1H | J = 13Hz | -OCH$_2$ CH$_2$ |
| 5.26 | d, d | 1H | J = 10Hz | -CH═CH$_2$ |
| 5.36 | t | 1H | J = 7Hz | 2' position-H |
| 5.40 | d, d | 1H | J = 17Hz | -CH═CH$_2$ |

-continued

¹H—NMR (270 MHz, CDCl₃)

| 5.51 | d | 1H | J = 1.5Hz | 5 position-H |
| 5.88–6.02 | m | 1H | | -C$\underline{H}$=CH₂ |

EXAMPLE 2

Synthesis of (1'R,2"R,5R,6S)-6-(1'-hydroxyethyl)-2-(2"-tetrahydrofuranyl)penem-3-carboxylic acid allyl ester (1'R,2"R,5R,6S)-6-(1'-tert-butyldimethylsilyloxyethyl)-2-(2"-tetrahydrofuranyl)penem-3-carboxylic acid allyl ester (6.59 g, 15 mmol) was dissolved in toluene (15 ml) and triethylamine trihydrogenfluoride (3.63 g, 22.5 mmol) was added to the resulting solution.

Thereafter, the solution was heated to 40° C. under stirring, which was continued for 4 h at the same temperature and for an additional 4 h at 50° C., whereby the reaction was completed. The reaction mixture was washed three times with water, once with 3% aqueous solution sodium hydrogencarbonate, and once with water, followed by drying on anhydrous magnesium sulfate. The dried solution was subjected to high-performance liquid chromatography by the internal standard method and by this quantitation, one could verify that the titled compound was contained in an amount of 4.45 g (yield: 91.2%).

EXAMPLE 3

Synthesis of (1'R, 2"R, 5R, 6S)-6-(1'-hydroxyethyl)-2-(2"-tetrahydrofuranyl)penem-3-carboxylic acid (5-methyl-2-oxo-1,3-dioxolen-4-yl)methyl ester

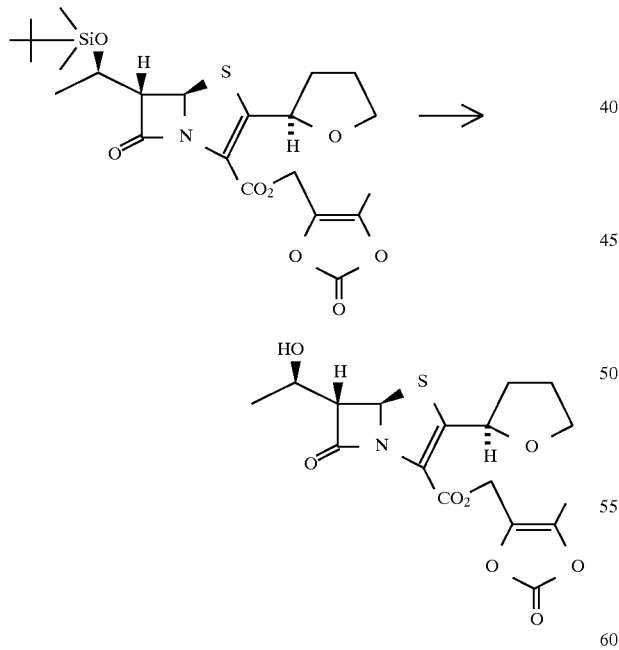

(1'R, 2"R, 5R, 6S)-6-[1'-(tert-butyldimethylsilyloxy)ethyl]-2-(2"-tetrahydrofuranyl)penem-3-carboxylic acid (5-methyl-2-oxo-1,3-dioxolen-4-yl)methyl ester (50 g) was dissolved in ethyl acetate (90 ml), followed by addition of a solution of triethylamine trihydrogenfluorides (24.4 ml) in ethyl acetate (8.5 ml). The resulting solution was stirred for 24 h at room temperature to complete the reaction. The reaction mixture was washed sequentially with water, aqueous solution of sodium hydrogencarbonate and brine, followed by addition n-hexane (58 ml) to allow a crystal to precipitate. The precipitated crystal was filtered and the titled compound was obtained as a colorless crystal in an amount 30.20 g (yield 77.8%; m.p.: 1.25°–130° C.).

IR(KBr) cm⁻¹:
3512 (—OH), 1840 (C=O of dioxolone), 1.796 (C=O in position 7), 1711 (C=O of ester in position 3).

NMR (CDCl₃/TMS) δ (ppm):
1.33 (3H, d, J=6.5 Hz, methyl of ethyl in position 6),
1.78–1.86 (1H, m, 1H in methylene of tetrahydrofuran ring),
1.93–2.08 (2H, m, methylene of tetrahydrofuran ring)
2.20 (3H, s, methyl of dioxolene)
2.41–2.48 (1H, m, 1H in methylene of tetrahydrofuran ring)
2.95 (1H,s,—OH)
3.72 (1H,dd,J=6.5,1.5 Hz, methine in position 6)
3.84–3.89 (1H,m,1H in methylene of tetrahydrofuran ring)
3.95–4.00 (1H,m,1H in methylene of tetrahydrofuran ring)
4.20 (1H,dq,J=6.5,6.5 Hz, methine of ethyl in position 6)
4.97 (2H,s, methylene attached to dioxolene)
5.30 (1H,t,J=7 Hz, methine of tetrahydrofuran ring)
5.51 (1H,d,J=1.5 Hz, methine in position 5)

According to the present invention, silylester compounds that are labile under strong acidic or basic conditions can be desilylated efficiently using inexpensive reagents.

What is claimed is:
1. A method of desilylating a silylether compound, which comprises reacting a silylether compound of the general formula (I):

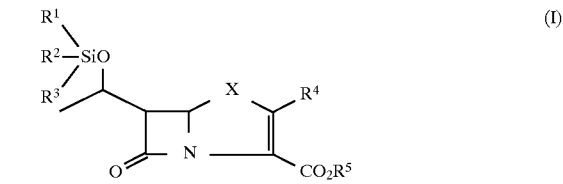

or a salt thereof where X is a methine substituted by an alkyl group having 1–3 carbon atoms, methylene or a sulfur atom; $R^1$, and $R^2$ and $R^3$ which may be the same or different are selected from the group consisting of an alkyl group having 1–6 carbon atoms, an alkoxy group having 1–6 carbon atoms, an aryl group having 6–10 carbon atoms and an aralkyl group having 6–10 carbon atoms; $R^4$ is selected from the group consisting of a hydrogen atom, a lower alkyl group, a lower alkylthio group, a lower alkoxy group, a 3–12 membered saturated or unsaturated monocyclic or polycyclic heterocyclic group having at least one hetero atom selected from the group consisting of oxygen, sulfur and nitrogen, a heterocyclic lower alkyl group wherein the heterocyclic part is a 3–12 membered saturated or unsaturated monocyclic or polycyclic heterocyclic group having at least one hetero atom selected from the group consisting of oxygen, sulfur and nitrogen, a heterocyclic thio group wherein the heterocyclic part is a 3–12 membered saturated or unsaturated monocyclic or polycyclic heterocyclic group having at least one hetero atom selected from the group consisting of oxygen, sulfur and nitrogen, a heterocyclic lower alkylthio group wherein the heterocyclic part is a 3–12 membered saturated or unsaturated monocyclic or polycyclic heterocyclic group having at least one hetero atom selected from the group consisting of oxygen, sulfur and nitrogen, an aryl group having 6–10 carbon atoms, an aryloxy group having 6–10 carbon atoms, an aralkyl group having 6–10 carbon atoms, lower alkyl, lower alkylthio, lower alkoxy, aryl, aryloxy and aralkyl groups substituted with one or more substituents selected from the group consisting of a halogen atom, a lower alkyl group, a lower alkoxy group, an acyloxy group having 2–11 carbon atoms, an amino group, an amino lower alkyl group, a carbamoyl group, a carbamoyloxy group, an imino lower alkylamino group, a 3–12 membered saturated or unsaturated monocyclic or polycyclic heterocyclic group having at least one hetero atom selected from the group consisting of oxygen, sulfur and nitrogen, and a heterocyclic lower alkyl group wherein the heterocyclic part is a 3–12 membered saturated or unsaturated monocyclic or polycyclic heterocyclic group having at least one hetero atom selected from the group consisting of oxygen, sulfur and nitrogen, and the above heterocyclic, heterocyclic lower alkyl, heterocyclic thio and heterocyclic lower alkylthio groups substituted with one or more substituents selected from the group consisting of a halogen atom, a lower alkyl group, a lower alkoxy group, a lower alkenyl group, an acyloxy group having 2–11 carbon atoms, an amino group, an amino lower alkyl group, a carbamoyl group, a carbamoyloxy group and an imino lower alkyl group; and $R^5$ is selected from the group consisting of a hydrogen atom and a carboxylic acid protecting group, with an amine hydrogen fluoride salt of the general formula (II):

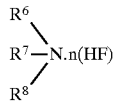
(II)

where $R^6$, $R^7$ and $R^8$ which may be the same or different are each an alkyl group having 1–8 carbon atoms; n is the number of hydrogen fluorides inherent in an amine salt of interest or a pyridine hydrogen fluoride salt of the general formula (III):

Py.p (HF)  (III)

where Py is pyridine or pyridine substituted with one or more substituents selected from the group consisting of a halogen atom, a lower alkyl group, a lower alkoxy group, a lower alkenyl group, an acyloxy group having 2–11 carbon atoms, an amino group, an amino lower alkyl group, a carbamoyl group, a carbamoyloxy group and an imino lower alkyl group; p is the number of hydrogen fluorides inherent in a pyridine salt of interest in an organic solvent that is inert to starting materials, end products and desilylating agents, thereby producing a compound of the general formula (IV):

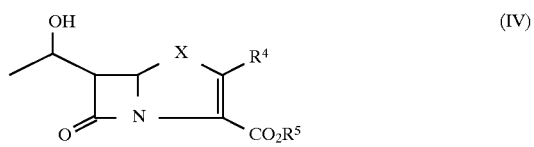

wherein X, $R^4$ and $R^5$ have the same meanings as defined above.

2. A method according to claim 1 wherein the amine hydrogen fluoride salt is triethylamine trihydrogenfluoride.

3. A method according to claim 1 wherein the pyridine hydrogen fluoride salt is pyridine polyhydrogenfluoride.

4. A method according to claim 1 wherein a silyl group in the silylether compound of the general formula (I) is a tert-butyldimethylsilyl group.

5. A method according to claim 1 wherein the silylether compound is a penem compound of the general formula (V):

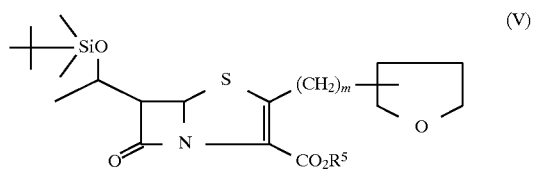

where $R^5$ has the same meaning as defined in claim 1; m is 0 or 1.

6. A method according to claim 1 wherein n is 3.

* * * * *

UNITED STATES PATENT AND TRADEMARK OFFICE
CERTIFICATE OF CORRECTION

PATENT NO. : 5,821,362

DATED : October 13, 1998

INVENTOR(s) : Akira KANEKO; Tsutomu KAKU; Masaji ISHIGURO; Takashi NAKATSUKA

It is certified that error appears in the above-identified patent and that said Letters Patent is hereby corrected as shown below:

On the Face of the Patent

[73] Assignee: Please add

--Nippon Soda Co., Ltd., Tokyo, Japan--

Signed and Sealed this

Twenty-second Day of August, 2000

Attest:

Q. TODD DICKINSON

*Attesting Officer*  *Director of Patents and Trademarks*